United States Patent
De Lanerolle et al.

(10) Patent No.: US 8,092,995 B2
(45) Date of Patent: Jan. 10, 2012

(54) EXPRESSED PSEUDOGENE REGULATES GENE EXPRESSION

(75) Inventors: Primal De Lanerolle, Oak Park, IL (US); Yoo Jeong Han, Skokie, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/651,810

(22) Filed: Jan. 4, 2010

(65) Prior Publication Data

US 2010/0173975 A1 Jul. 8, 2010

Related U.S. Application Data

(60) Provisional application No. 61/142,259, filed on Jan. 2, 2009.

(51) Int. Cl.
*C12Q 1/68* (2006.01)
(52) U.S. Cl. .......................................................... 435/6
(58) Field of Classification Search ........................ 435/6
See application file for complete search history.

(56) References Cited

U.S. PATENT DOCUMENTS 7,186,512 B2 * 3/2007 Martienssen et al. ............. 435/6
2006/0211017 A1 * 9/2006 Chinnaiyan et al. ............. 435/6

OTHER PUBLICATIONS

Trask, Barbara, et al. "Large multi-chromosomal duplications encompass many members of the olfactory receptor gene family in the human genome" Human Molecular Genetics, Oxford University Press, vol. 7, No. 13 (1998) pp. 2007-2020.
"MYLK Myosin Light Chain Kinase" Entrez Gene, GeneID: 4638, updated Dec. 26, 2009.
"MYLKP Myosin Light Chain Kinase Pseuodene" Entrez Gene, GeneID: 9430, updated Jun. 25, 2009.
"Homo sapiens myosin light chain kinase (MLCK) mRNA, complete cds", GenBank: U48959.2, dated Mar. 14, 2000.
Gao, Li, et al."Novel Polymorphisms in the Myosin Light Chain Kinase Gene Confer Risk for Acute Lung Injury" American Journal of Respiratory Cell and Molecular Biology, vol. 34. pp. 487-495 (2006).
"Homo sapiens chromosome 3, olfactory receptor pseudogene cluster 1, complete sequence, and myosin light chain kinase (MLCK) pseudogene, partial sequence", GenBank: AF042089.1, dated Nov. 2, 2000.
Lazar V, Garcia JG "A single human myosin light chain kinase gene (MLCK; MYLK)" Genomics, Apr. 15, 1999. pp. 256-267.
"Homo sapiens myosin light chain polypeptide kinase isoform 1 (MYLK) mRNA, complete cds, alternatively spliced", GenBank: AY424270.1, dated Dec. 23, 2004.
"Homo sapiens myosin light chain polypeptide kinase isoform 2 (MYLK) mRNA, complete cds, alternatively spliced", GenBank: AY424269.1, dated Dec. 23, 2004.
"Homo sapiens long myosin light chain kinase mRNA, complete cds", GenBank: AY339601.1, dated Apr. 19, 2004.
"Homo sapiens myosin light chain kinase isoform 2 (MLCK) mRNA, complete cds", GenBank: AF069601.2 dated Mar. 14, 2000.
Brand-Arpon, Veronique, et al. "A Genomic Region Encompassing a Cluster of Olfactory Receptor Genes and a Myosin Light Chain Kinase (MYLK) Gene is Duplicated on Human Chromosome Regions 3q13-q21 and 3p13" Genomics vol. 56, pp. 98-110 (1999).
Han, Yoo-Jeong, et al. "Naturally Extended CT AG Repeats Increase H-DNA Structures and Promoter Activity in the Smooth Muscle Myosin Light Chain Kinase Gene" Molecular and Cellular Biology, pp. 863-872, Jan. 2008.
Han, Y. "Pseudo Myosin Light Chain Kinase (MLCK) Gene Transcribes in Cancerous Tissues and Cells", American Society of Human Genetics, 2008 meeting abstract #241.
Gu, L.Z., et al. Inhibiting myosin light chain kinase retards the growth of mammary and prostate cancers cells. Eur. J. Cancer. 2006 47:948-57 (abstract only).

\* cited by examiner

*Primary Examiner* — Brian Whiteman
(74) *Attorney, Agent, or Firm* — Banner & Witcoff, Ltd.

(57) ABSTRACT

Selective expression of a pseudogene of myosin light chain kinase is found in cancer cells and tissues but not in normal cells and tissues. The pseudogene is expressed, and when expressed it inhibits expression of the ancestral myosin light chain kinase. This widespread expression among cancer cell types and the selective expression in cancer cells versus normal cells opens the door to many diagnostic and therapeutic applications.

7 Claims, 7 Drawing Sheets

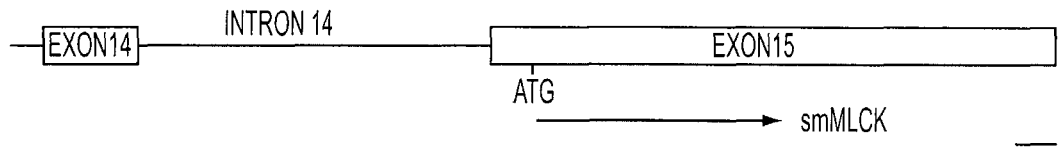

FIG. 7A

```
              ....|....|....|....|....|....|....|....|....|....|....|....|
                 -433       -423       -413       -403       -393       -383
WKY      gtgagtgccc ccaggagaag cctagccagg tctcccacac tcacccgcca tcctctgCct
SHR      gtgagtgccc ccaggagaag cctagccagg tctcccacac tcacccgcca tcctctgtct
                             5´ PRIMER
              ....|....|....|....|....|....|....|....|....|....|....|....|
                 -373       -363       -353       -343       -333       -323
WKY      ggccctgaag cctggggttg tttgtgtcct cctgttaagt ctgccagagc caaagagaaa
SHR      ggccctgaag cctggggttg tttgtgtcct cctgttaagt ctgccagagc caaagagaaa
         Ap-2αA
              ....|....|....|....|....|....|....|....|....|....|....|....|
                 -313       -303       -293       -283       -273       -263
WKY      gattggaaag ggatgaaggg gagaggccag aagaaggcaa aggaggggt gatgtgtgtt
SHR      gattggaaag ggatgaaggg gagaggccag aagaaggcaa aggaggggt gatgtgtgtt
                    c-Ets-1
              ....|....|....|....|....|....|....|....|....|....|....|....|
                 -253       -243       -233       -223       -213       -203
WKY      tctttttcCt ctctctctct ctctctctct ctctctctct ct--------
SHR      tcttttcttt ctctctctct ctctctctct ctctctctct ctctctctct
                             CT REPEATS                    INSERTION
              ....|....|....|....|....|....|....|....|....|....|....|....|
                 -193       -183       -173       -163       -153       -143
WKY      ----ttgcac acaccttat aaggctactg aaatcattac cgatataata aaccaactag
SHR      ctctttgcac acaccttat aaggctactg aaatcattac cgatataata aaccaactag
                             CArG BOX
              ....|....|....|....|....|....|....|....|....|....|....|....|
                 -133       -123       -113       -103        -93        -83
WKY      gcaagtgagt ccctctcacc aatgttccct tctataaaca cagcctggcc ggcccccacg
SHR      gcaagtgagt ccctctcacc aatgttccct tctataaaca cagcctggcc ggcccccacg
                        C-Myb             TATA BOX       Ap-2αA
              ....|....|....|....|....|....|....|....|....|....|....|....|
                  -73        -63        -53        -43        -33         23
WKY      tccTcttccc ccctcctctc taccctccgc cctcagggat ttgctctccc ctgacgtttc
SHR      tccccttccc ccctcctctc taccctccgc cctcagggat ttgctctccc ctgacgtttc
                  c-Ets-2                                  ATF-1
              ....|....|....|....|....|....|....|....|....|....|....|....|
                  -13         -3         +1         +8        +18        +28        +38
WKY      tgtcttaccc agcccctttt Actccctgct actttctctt tttccttcac tggttattgc
SHR      tgtcttaccc agcccctttt cctccctgct actttctctt tttccttcac tggttattgc
                                                              3´ Primer WKY      ag
SHR      ag
```

EXPRESSED PSEUDOGENE REGULATES GENE EXPRESSION

This application claims the benefit of and incorporates the content of provisional application Ser. No. 61/142,259 filed Jan. 2, 2009.

This invention was made with government support under NIH RO1 HL 59618 and NIH RO1 HL 64702 awarded by the National Institutes of Health. The government has certain rights in the invention.

TECHNICAL FIELD OF THE INVENTION

This invention is related to the area of cancer diagnostics and therapeutics. In particular, it relates to use of the pseudogene of MYLK.

BACKGROUND OF THE INVENTION

Pseudogenes have been defined as nonfunctional genomic sequences that are originally derived from paralogous functional genes. Although the biological importance of pseudogenes is not clear, pseudogenes have been widely used as evolution fossils. During the evolution to higher primates, a functional MYLK (myosin light chain kinase) gene was partially duplicated, making a pseudo-MYLK (MYLKP) gene in humans, chimpanzees, and gorillas. MLCK (myosin light chain kinase protein) is of critical importance in regulating cytoskeletal dynamics that are necessary for cell division and metastasis by increasing myosin-actin cross-bridges A functional gene encoding MLCK, namely MYLK, is located on chromosome 3q21, spanning over 270 kb and containing at least 34 exons that encode 3 proteins: non-muscle MLCK (nmMLCK, 220 kDa), smooth muscle MLCK (smMLCK, 130 kDa) and Telokin (20 kDa). The nmMLCK is translated from exon 1 to exon 34 while the smMLCK is translated from exon 18 to exon 34. A number of isoforms resulting from different splicing patterns are also known. A pseudo-MYLK gene, in contrast, is located on chromosome 3p12, and contains only 5 exons which correspond to exons 13-17 of the functional gene. See Brand-Arpon et al., "A genomic region encompassing a cluster of olfactory receptor genes ad a myosin light chain kinase (MYLK) gene is duplicated on human chromosome regions 3q13-q21 and 3p13" *Genomics* 56, 98-110, 1998.

There is a continuing need in the art to identify techniques which can detect cancer early in the general population and agents which can effectively inhibit the growth or stimulate the death of cancer cells.

SUMMARY OF THE INVENTION

According to one aspect of the invention a method aids in detecting a malignancy in a human. A body sample of the human is tested for the presence of an expression product of pseudogene MYLKP (myosin light chain kinase). The body sample is selected from the group consisting of blood, serum, and plasma. The human is identified as likely to have a malignancy if the expression product is present and detected in the body sample.

Another aspect of the invention is an isolated RNA molecule that is expressed from pseudogene MYLKP (myosin light chain kinase).

An additional aspect of the invention is a method of treating a primate that has a malignancy. The primate is selected from the group consisting of human, chimpanzee, and gorilla. A specific inhibitor of nmMYLK (non-muscle myosin light chain kinase) expression or enzyme activity is administered to the primate. The inhibitor induces death or growth arrest in malignant cells of the primate selectively relative to non-malignant cells.

Yet another aspect of the invention is a method to aid in detecting a malignancy in a human. A tissue sample of the human suspected of being malignant is tested for the protein expression product of smMYLK. The tissue sample is identified as likely to be malignant if the protein expression product is down-regulated relative to a control tissue of the human.

An aspect of the invention is a method to screen for drug candidates potentially useful for treating malignancy in a primate selected from the group consisting of human, chimpanzee, and gorilla. Primate cells selected from the group consisting of human, chimpanzee, and gorilla cells are treated with a test substance. The treated cells are assayed to determine relative expression of nmMYLK and smMYLK. A test substance is identified as a drug candidate potentially useful for treating malignancy if the test substance selectively inhibits expression of nmMYLK relative to smMYLK.

Another aspect of the invention is a method to screen for drug candidates potentially useful for treating malignancy in a primate selected from the group consisting of human, chimpanzee, and gorilla. Proteins nmMLCK and smMLCK are contacted with a test substance. The proteins are selected from the group consisting of human, chimpanzee, and gorilla proteins. The proteins are assayed to determine relative activity of the proteins in the presence and in the absence of the test substance. A test substance is identified as a drug candidate potentially useful for treating a malignancy if the test substance selectively inhibits nmMLCK activity relative to smMLCK activity.

An additional aspect of the invention is a fusion construct useful for obtaining cancer-specific expression. A promoter from pseudogene MYLKP is operably linked to a coding sequence for a cytotoxic product. The product may be a fusion protein or a singleton cytotoxic protein.

These and other embodiments which will be apparent to those of skill in the art upon reading the specification provide the art with additional tools for diagnosing and treating cancers in higher primates.

BRIEF DESCRIPTION OF THE DRAWINGS

FIGS. 7A-7B show isolation and analysis of intron 14 of the rat MYLK gene. (FIG. 7A) Exon-intron structure of the rat smMLCK gene. The translation start site of the smMLCK in exon 15 is shown (ATG). (FIG. 7B) DNA sequences of intron 14 from SHR (SEQ ID NO: 3) and WKY (SEQ ID NO: 4) rats. Intron 14 was isolated from genomic DNA from SHR and WKY rats using PCR. DNA sequences of the 5' and 3' primers are shown (italics, underlined). The transcription start site (+1) of smMLCK was identified using primer extension and 5' RACE. Analysis of transcription elements using the Transcription Element Search System identified >55 elements, including SRF (CArG box) and TBP (TATA box) binding sites. Comparison of these sequences revealed the presence of a 12-base pair insertion (Insertion) in the SHR sequence not found in the WKY sequence.

DETAILED DESCRIPTION OF THE INVENTION

Figure 1:
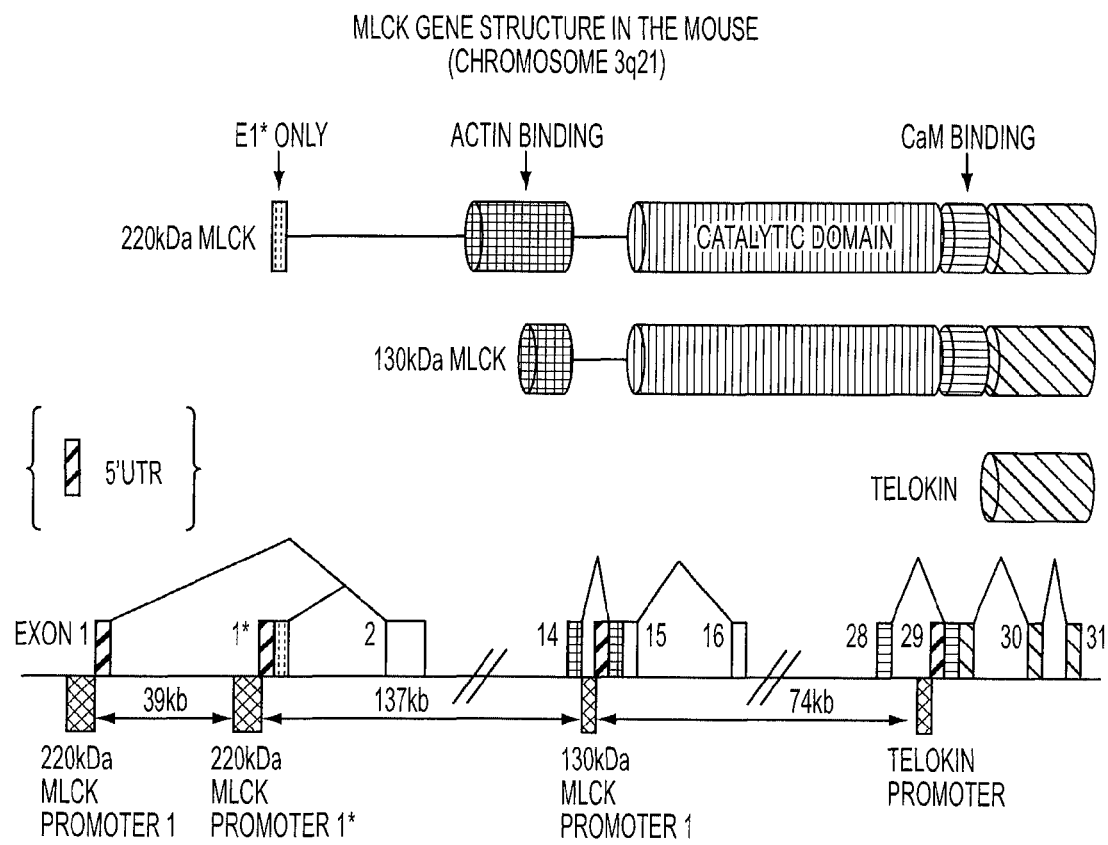
FIG. 1 shows the MYLK gene structure in the mouse, including three proteins and four promoters.

The inventors have discovered that the pseudo-gene MYLKP has a functional promoter for smMLCK at the intron between exons 17-18 and transcribes at least a part of the gene for smMYLK. We performed reverse transcriptase PCR (RT-PCR) and Northern blot analyses using RNAs purified from various human cancerous and non-cancerous tissues. In humans with no cancer, none of tissues or cultured cells expressed the pseudo-MYLK. However, all of the cancerous tissues and cell lines that we have tested express mRNA from MYLKP. These data strongly suggest that the MYLKP gene is selectively expressed in the development of cancers. This is, to the best of our knowledge, the first association of pseudogene expression with human disease. Pseudogenes, in general, may be important in the development of a variety of human diseases.

We have further found that the expression of the smooth muscle MLCK is greatly reduced in cells that express the pseudogene. The combined findings of cancer-selective expression and the negative effects of inhibiting smooth muscle MLCK on cell motility and cell survival, provide an opportunity for differential expression and effects in cancer versus normal cells.

The MYLKP gene is found in all higher primates except the gibbon. It is found in humans, chimpanzees, and gorillas. The pseudogene is the result of gene duplication, not a retrotransposition. Brand-Arpon et al. report that the pseudogene contains several deleterious mutations. It contains a frame shift mutation that results in multiple stop codons and a potential 45 amino acid residue protein.

Types of cancers in which expression of pseudo-MLCK has been found are cervical, leukemia, uterus, colon, bladder, lymph node, and vulva. Because of the breadth of these tumor types, other types as well are expected to be involved, including, breast, prostate, brain, head and neck, liver, pancreas, testes, kidney, lung, bone.

When testing a body sample for the presence of an expression product of pseudogene MYLKP (myosin light chain kinase), either a protein based or an RNA based assay can be used. If an RNA based assay is used, typically a reverse transcription reaction will be used, followed by an amplification reaction. These reactions are known in the art and any of a variety can be used, including but not limited to polymerase chain reaction, rolling circle amplification, emulsion amplification, and solid phase amplification. Products can be identified by any means known in the art, including size-based means, such as gel electrophoresis. The body sample may be blood, serum, or plasma, or fractions or processed samples from these sources. Alternatively other body fluids including lymph, urine, tears, saliva, sputum, stool, can be tested. The human is identified as likely to have a malignancy if the expression product is present and detected in the body sample. Control samples from one or more individuals who do not have cancer or who are not suspected of having cancer may be used. This may be based on medical history, or any other technical assessment, including CT scans, MRI scans, blood tests, etc.

An isolated RNA molecule that is expressed from pseudogene MYLKP (myosin light chain kinase) can be obtained by isolation from natural expressing cells or from cells that are engineered to express the pseudogene. For example lentivirus constructs can be used to infect cells, and the RNA can be isolated from the infected cells. The appropriate RNA molecules can be isolated by hybridization to probes. Suitable probes can be designed based on the sequences of the pseudogene. Alternatively, RNA molecules can be transcribed in vitro or synthesized. The RNA molecule will typically be at least 18, at least 20, at least 30, at least 50, at least 75, at least 100, at least 150 ribonucleobases in length.

Primates, particularly those that express the pseudogene MYLKP and that have a malignancy can be treated using a specific inhibitor of nmMYLK (non-muscle myosin light chain kinase) expression or enzyme activity. The inhibitor induces death or growth arrest in malignant cells of the primate selectively relative to non-malignant cells. Typically the inhibitor will be one that is complementary to the 5'-portions of the nmMLCK transcript but not to the smMLCK transcript. The inhibitor may be an inhibitory RNA such as an siRNA, an antisense RNA, and RNAi, etc. Alternatively the inhibitor may specifically bind to the promoter of the nmMLCK transcript but not to the promoter of the smMLCK transcript. Binding may be based on sequence complementarity. Alternatively, the inhibitor may be an antibody that is specific for epitopes that are found in the N-terminal portion of the actin binding domain, i.e., epitopes that are not found in the smMLCK protein.

The nmMLCK protein is 1914 amino acids in humans, whereas the smMLCK is 991 amino acids. See Lazar and Garcia, Genomics 1999, 57:256-67 and Brand-Arpon, 1999, supra. The MYLKP is described under GeneID: 9430 (NCBI, NLM). See also, GenBank U48959 and GenBank AF042089. The sequence information in these publicly available documents are incorporated by reference herein.

Another way to detect a malignancy in a human involves testing a tissue sample suspected of being malignant. The protein expression product of smMYLK is detected using any technique that can identify it. This may involve an antibody or an enzyme assay, for example. It may additionally involve a separation technique such as in an immunoblot. Down-regulation of smMYLK can be assessed relative to a control tissue of the human.

Drug candidates potentially useful for treating a malignancy in a primate can be screened by treating cells of a primate with a test substance. The treated cells are assayed to determine relative expression of nmMYLK and smMYLK. A test substance is identified as a drug candidate potentially useful for treating malignancy if the test substance selectively inhibits expression of nmMYLK relative to smMYLK or relative to telokin or both. Expression can be assayed by any means known in the art including but not limited to a Western blot, a Northern blot, and an antibody, a hybridization technique and/or a reverse transcriptase-polymerase chain reaction.

Drug candidates can also be screened for potentially useful substances for treating malignancy in a primate by contacting proteins nmMLCK and smMLCK with a test substance. The proteins are assayed to determine relative activity of the proteins in the presence and in the absence of the test substance. A test substance is identified as a drug candidate potentially useful for treating a malignancy if the test substance selectively inhibits nmMLCK activity relative to smMLCK activity.

Fusion constructs may be used to obtain cancer-specific expression. A promoter from pseudogene MYLKP can be operably linked to a nucleic acid coding sequence for a cytotoxic product. The product may be a fusion protein or a singleton cytotoxic protein. The toxin may be for example a biological toxin such as shiga toxin, clostridium toxin, pseudomonas toxin. The toxin may be an enzyme that converts a pro-drug to a cytotoxic drug. Nucleic acid constructs which encode the fusion protein or singleton cytotoxic protein or enzyme may also be useful as a means of administration and introduction of the encoded protein to a cell in the body. Optionally, an upstream transcription regulatory region from MYLKP can be used in the fusion construct to obtain or enhance tumor specific expression.

EXAMPLE 1

Characterization of the smMLCK Promoter in Humans

Figure 5:
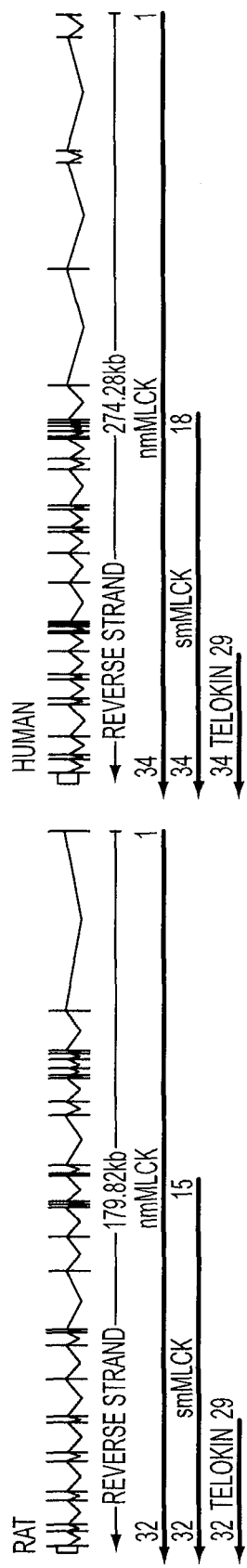
FIG. 5 shows the structure of MYLK gene in rats and human. Note that smMLCK is encoded by exons 15-32 in rats while it is encoded by exons 18-34 in humans.

In humans, a single functional human MYLK gene (GenBank Accession Number U48959) (1,2) is located on chromosome 3qcen-q21. It spans >272 kb and contains at least 34 exons (1-3) while the rat MYLK gene contains 32 exons and spans 177 Kb (FIG. 5). Both code for 3 proteins, non-muscle MLCK (nmMLCK), smooth muscle MLCK (smMLCK) and telokin. In humans, nmMLCK, smMLCK and telokin are transcribed by exons 1-34 (4), exons 18-34 and exons 29-34 (5), respectively.

Figure 3:
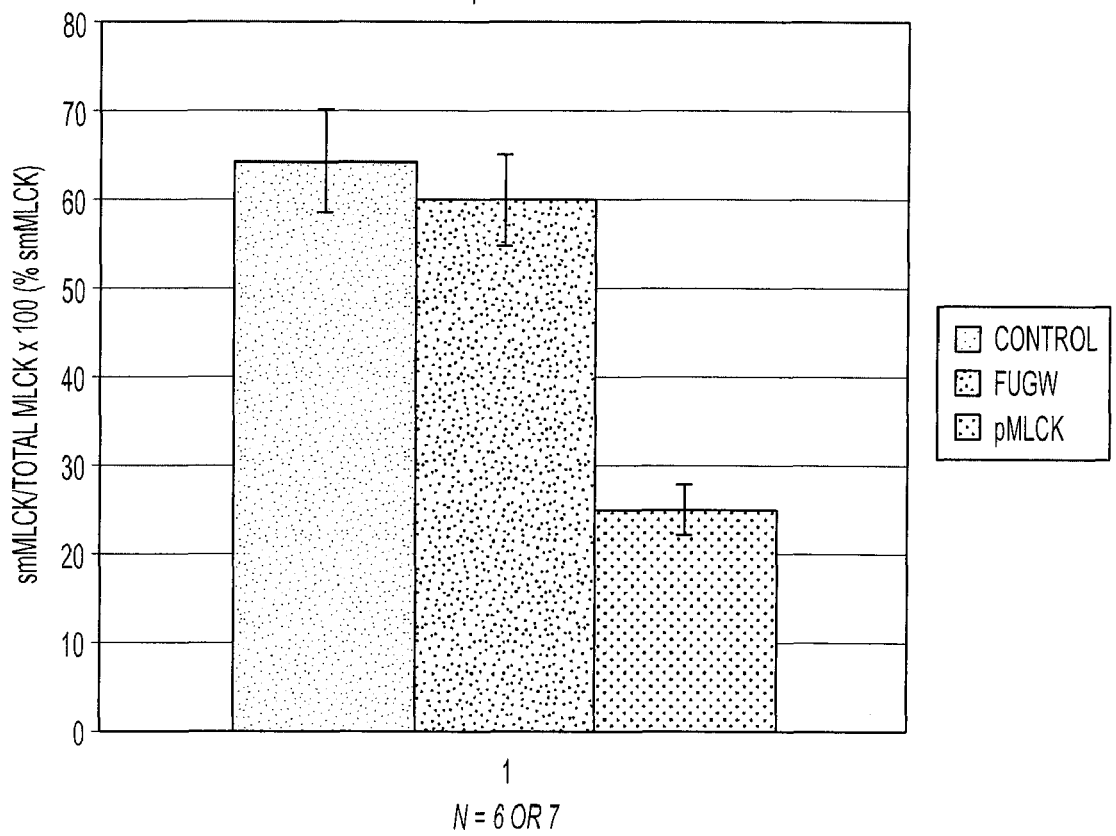
FIG. 3 shows quantitation of smooth muscle MLCK expression in HUF cells infected with the pseudogene in a lentivirus or control lentivirus. Smooth muscle MLCK is expressed as a fraction of total MLCK.
Figure 6:
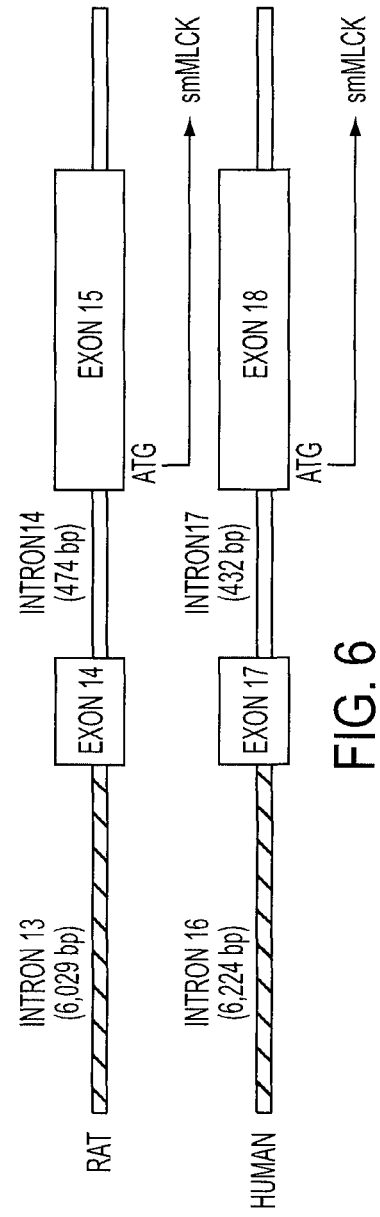
FIG. 6 shows the exon-intron structure in rat and human MYLK genes. The smMLCK is translated from the start codon (ATG) located in exon 15 and exon 18 of the rat and human genes. The introns preceding the start codons have promoter elements controlling the expressions of smMLCK.
Figure 8:
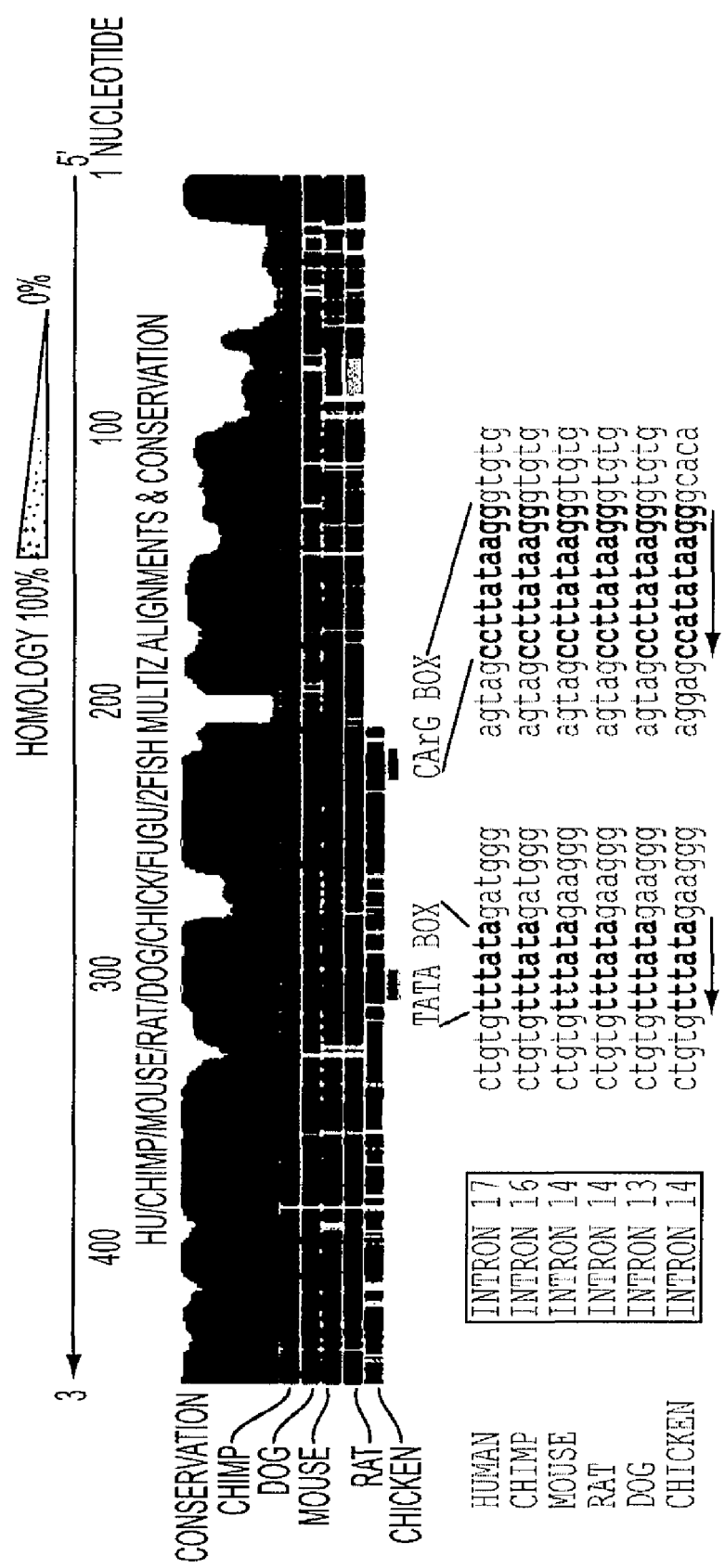
FIG. 8 shows homology analysis of the intron 17 of the human MYLK gene among species. The blue arrow indicates the orientation of DNA sequences (3'<- 5') and the blue letters indicate the positions of nucleotides. Darkness gradients from black to white represent homology from 100% - 0%. The DNA sequences around TATA (SEQ ID NO: 5, 7, 9, 11, 13, and 15) and CArG (SEQ ID NO: 6, 8, 10, 12, 14, and 16) box are from the antisense strand of MYLK gene, showing reverse complementary sequences. Note that DNA sequences of intron 17 in humans are highly conserved among the species. Human (SEQ ID NO: 5 and 6), chimpanzee (SEQ ID NO: 7 and 8), mouse (SEQ ID NO: 9 and 10), rat (SEQ ID NO: 11 and 12), dog (SEQ ID NO: 13 and 14), chicken (SEQ ID NO: 15 and 16).

Analysis of the exon-intron structure in the human MYLK gene using EMBL Ensembl (Transcript ENST00000360304) showed that smMLCK is encoded from exon 18 through exon 34 and the translation start site (ATG) for smMLCK is located in exon 18 (FIG. 6). We have extensively characterized intron 14 in normotensive and hypertensive rats (6) and shown that it contains TATA and CArG elements typical of promoters. Comparing the human and rat genes revealed that the intron preceding exon 18 (intron 17) in humans has the same promoter elements as intron 14 in rats (FIG. 7) (See FIG. 3 of reference 6). Therefore, we performed comparative analyses of the DNA sequences found in various vertebrate species using the UCSC genome browser (FIG. 8). This analysis was based on the hypothesis that important regulatory elements of a promoter are conserved between species due to functional constraints. It showed that the promoter sequences of human intron 17 are highly conserved among chimps, dogs, mice, chickens and rats (FIG. 8). Importantly, the TATA and CArG elements are 100% conserved among these species.

We, therefore, isolated intron 17 from genomic DNA obtained from HeLa cells using a PCR method, cloned it into a pGL3B-firefly luciferase reporter gene and transfected A7r5 rat aorta smooth muscle cells using Fugene transfection system (Roche). The luciferase assay showed that the intron 17 promoter from HeLa cells has relatively strong activity compared to empty pGL3B reporter gene (2,392±320). The activities of the human and rat promoters, 18,510±3,168 and 15,951±2,137 relative units, respectively, were very similar. Importantly, these data established that intron 17 contains the promoter for the human smMLCK gene.

EXAMPLE 2

Figure 2:
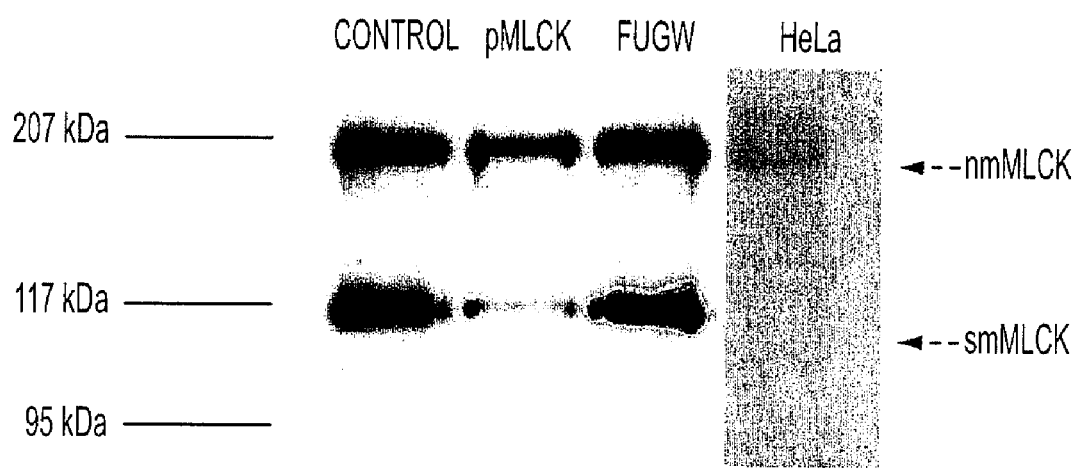
FIG. 2 shows expression of MLCK proteins in the presence of expressed pseudogene in human uterine fibroblast cells. Pseudogene expression decreases smooth muscle MLCK expression.

Expression of MLCK Proteins in the Presence of Expressed Pseudogene in Human Uterine Fibroblast Cells Control human uterine fibroblasts (HUF cells), HUF cells infected with a control lentivirus (FUGW) or pMYLK lentivirus or HeLa cells grown in culture were washed in PBS and extracted in 9M urea, 5 mM DTT, 20 mM Tris, pH 7.5. The cell extracts were collected by centrifugation and the protein concentration was determined. Approximately 50 μg of cell extract were incubated with one third of the volume of 3% SDS, 50 mM β-mercaptoethanol, 30% glycerol, 150 mM Tris, pH 6.7 for 30 minutes at room temperature and applied to a 7.5% polyacrylamide gel. The proteins were transferred to nitrocellulose, probed with an affinity purified antibody to MLCK and the immunoreactive bands were visualized using enhanced chemiluminescence (ECL, Roche). The bands were quantified densitometrically and ratio of the band representing smMLCK to total MLCK (smMLCK plus nmMLCK) was calculated. The data represent an N=6-7. The error bars indicate the standard error of the mean. See FIG. 2.

EXAMPLE 3

Quantitation of Smooth Muscle MLCK Expression in HUF Cells Infected with the Pseudogene in a Lentivirus or Control Lentivirus Control human uterine fibroblasts (HUF cells), HUF cells infected with a control lentivirus (FUGW) or pMYLK lentivirus were analyzed by western blotting as described above. The bands were quantified densitometrically and ratio of the band representing smMLCK to total MLCK (smMLCK plus nmMLCK) was calculated. The data represent N=6-7. The error bars indicate the standard error of the mean. See FIG. 3.

EXAMPLE 4

Figure 4:
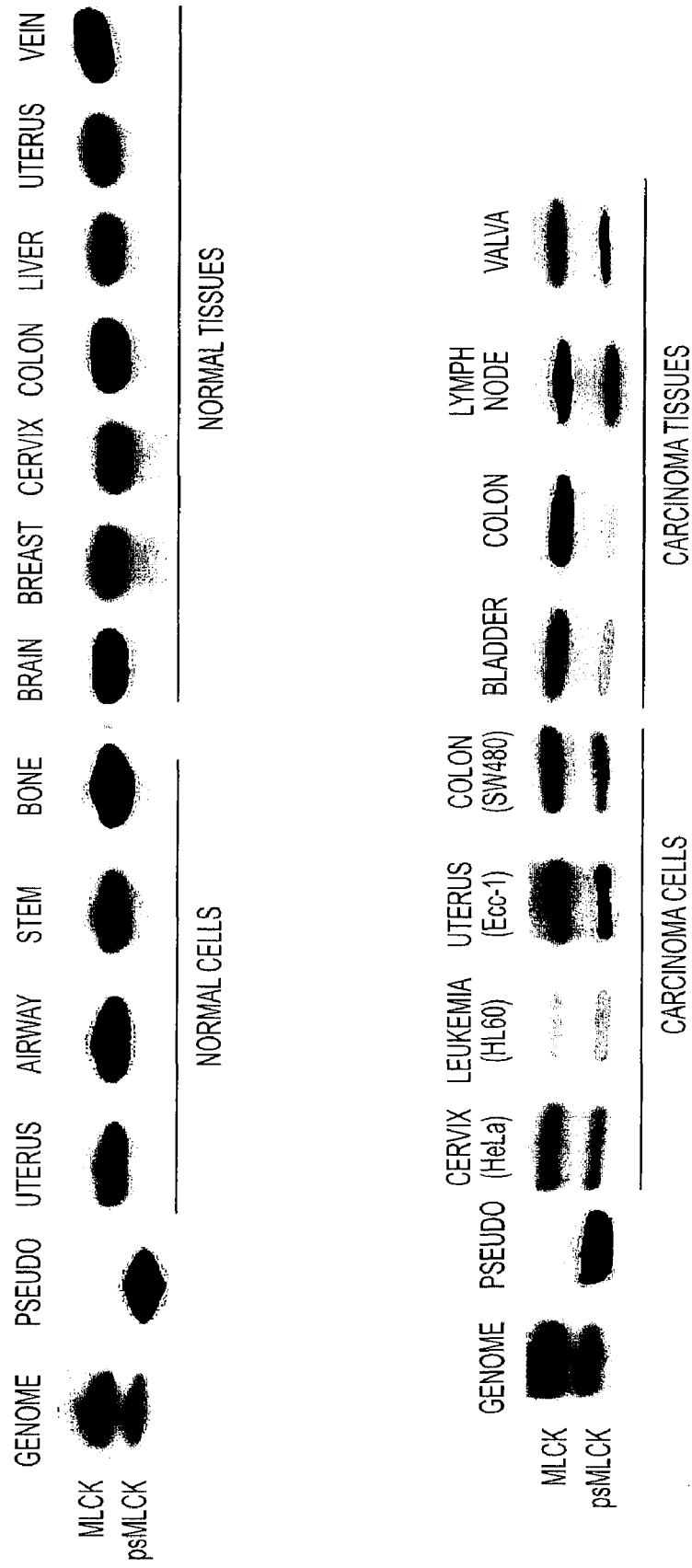
FIG. 4 shows that MYLKP mRNA is only expressed in cancer cells or tissue and not in normal cells.

MYLKP mRNA is Only Expressed in Cancer Cells or Tissue and not in Normal Cells Quantitative PCR was performed on various human normal and cancer cells and tissues using the following primer set: 5' TGA ACT TGG TGG TCT TGA GG 3' (SEQ ID NO: 1) and 5' ATG GAT CTC CGT GCC AAC C 3'(SEQ ID NO:2). One of the primers was radiolabeled to increase the sensitivity. DNA (40 ng) was incubated with 1 μM of each primer, TAG DNA polymerase. The PCR reaction was run for 17 cycles and the PCR products were analyzed on a 1.5% agarose gel and analyzed using a phosphorimager. Because the primers flank a region of MYLK and corresponding region of MYLKP that contains a 73 by deletion, the predicted PCR products for the MYLK and MYLKP are 667 and 594 bp, respectively. See FIG. 4.

REFERENCES

All cited references are expressly incorporated herein.

1. Potier, M. C., Chelot, E., Pekarsky, Y., Gardiner, K., Rossier, J. and Turnell, W. G. The human myosin light chain kinase (MLCK) from Hippocampus: Cloning, sequencing, expression, and localization to 3qcen-q21. Genomics 29, 562-570, 1995.

2. Garcia, J., Lazar, V., Gilbert-McClain, L., Gallagher, P., and Verin, A. Myosin light chain kinase in endothelium: Molecular cloning and regulation. Am. J. Respir. Cell Mol. Biol. 16: 489-494, 1997.

3. Watterson, D. M., Schavocky, J. P., Guo, G., Weiss, C., Chlenski, A., Shirinsky, V. P., Van Eldik, L. J. and Haiech, J. Analysis of the kinase related protein gene found at human chromosome 3q21 in a multi gene cluster: organization, expression, alternative splicing, and polymorphic marker. J. Cell. Biochem. 75: 481-491, 1999.

4. Gallagher, P. J., Herring, B. P. and Stull, J. T. Myosin light chain kinases. J. Muscle. Res. Cell. Motil. 18: 1-16 (1997)

5. Gallagher, P. J., and Herring, B. P. The carboxyl terminus of the smooth muscle myosin light chain kinase is expressed as an independent protein, telokin. J. Biol. Chem. 266: 23945-52, 1991.

6. Han, Y. J., Hu, W. Y., Chernaya, O., Antic, N., Gu, L., Gupta, M., Piano, M. and de Lanerolle, P. Increased myosin light chain kinase expression in hypertension: Regulation by SRF via an insertion mutation in the promoter. Mol. Biol. Cell. 17: 4039-50, 2006.

The invention claimed is:

1. A method to aid in detecting a malignancy in a human, comprising the steps of:
   testing a body sample of the human for the presence of an expression product of MYLKP (myosin light chain kinase pseudogene), wherein the body sample is selected from the group consisting of blood, serum, plasma, and tissue sample suspected of being malignant; and
   identifying the human as likely to have a malignancy if the expression product is present.

2. The method of claim 1 wherein the expression product in an RNA.

3. The method of claim 1 wherein the step of testing comprises hybridization.

4. The method of claim 1 wherein the step of testing comprises amplification.

5. The method of claim 1 wherein the step of testing comprises a size measurement.

6. The method of claim 1 wherein the pseudogene is at chromosome 3p13.

7. The method of claim 1 wherein the amount of the expression product is compared to a control sample from one or more humans that do not have a malignancy.

* * * * *

```
                        SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
tgaacttggt ggtcttgagg                                                    20

<210> SEQ ID NO 2
<211> LENGTH: 19
<212> TYPE: DNA
<213> ORGANISM: Homo sapiens

<400> SEQUENCE: 2
atggatctcc gtgccaacc                                                     19

<210> SEQ ID NO 3
<211> LENGTH: 470
<212> TYPE: DNA
<213> ORGANISM: Rattus rattus

<400> SEQUENCE: 3
gtgagtgccc ccaggagaag cctagccagg tctcccacac tcacccgcca tcctctgcct        60
ggccctgaag cctggggttg tttgtgtcct cctgttaagt ctgccagagc caaagagaaa       120
gattggaaag ggatgaaggg gagaggccag aagaaggcaa aggaggggt gatgtgtgtt        180 tcttttcct ctctctctct ctctctctct ctctctctct ctctctctct ctttgcacac       240
acccttataa ggctactgaa atcattaccg atataataaa ccaactaggc aagtgagtcc       300
ctctcaccaa tgttcccttc tataaacaca gcctggccgg ccccacgtc ctcttccccc       360 ctcctctcta ccctccgccc tcagggattt gctctcccct gacgtttctg tcttacccag       420
ccccttttac tccctgctac tttctctttt tccttcactg gttattgcag                  470

<210> SEQ ID NO 4
<211> LENGTH: 482
<212> TYPE: DNA
<213> ORGANISM: Rattus rattus

<400> SEQUENCE: 4
gtgagtgccc ccaggagaag cctagccagg tctcccacac tcacccgcca tcctctgtct        60
ggccctgaag cctggggttg tttgtgtcct cctgttaagt ctgccagagc caaagagaaa       120
```

```
gattggaaag ggatgaaggg gagaggccag aagaaggcaa aggagggggt gatgtgtgtt    180 tcttttttctt ctctctctct ctctctctct ctctctctct ctctctctct              240
ctctttgcac acacccttat aaggctactg aaatcattac cgatataata aaccaactag   300
gcaagtgagt ccctctcacc aatgttccct tctataaaca cagcctggcc ggcccccacg   360
tccccttccc ccctcctctc taccctccgc cctcagggat ttgctctccc ctgacgtttc   420
tgtcttaccc agcccctttt cctccctgct actttctctt tttccttcac tggttattgc   480
ag                                                                    482
```

```
<210> SEQ ID NO 5
<211> LENGTH: 17
<212> TYPE: DNA
<213> ORGANISM: Homo sapiens

<400> SEQUENCE: 5
ctgtgtttat agatggg                                                    17

<210> SEQ ID NO 6
<211> LENGTH: 20
<212> TYPE: DNA
<213> ORGANISM: Homo sapiens

<400> SEQUENCE: 6
agtagcctta taagggtgtg                                                 20

<210> SEQ ID NO 7
<211> LENGTH: 17
<212> TYPE: DNA
<213> ORGANISM: Pan troglodytes

<400> SEQUENCE: 7
ctgtgtttat agatggg                                                    17

<210> SEQ ID NO 8
<211> LENGTH: 20
<212> TYPE: DNA
<213> ORGANISM: Pan troglodytes

<400> SEQUENCE: 8
agtagcctta taagggtgtg                                                 20

<210> SEQ ID NO 9
<211> LENGTH: 17
<212> TYPE: DNA
<213> ORGANISM: Mus musculus

<400> SEQUENCE: 9
ctgtgtttat agaaggg                                                    17

<210> SEQ ID NO 10
<211> LENGTH: 20
<212> TYPE: DNA
<213> ORGANISM: Mus musculus

<400> SEQUENCE: 10
agtagcctta taagggtgtg                                                 20

<210> SEQ ID NO 11
<211> LENGTH: 17
<212> TYPE: DNA
<213> ORGANISM: Rattus rattus
```

-continued

```
<400> SEQUENCE: 11
ctgtgtttat agaaggg                                                   17

<210> SEQ ID NO 12
<211> LENGTH: 20
<212> TYPE: DNA
<213> ORGANISM: Rattus rattus

<400> SEQUENCE: 12
agtagcctta taagggtgtg                                                20

<210> SEQ ID NO 13
<211> LENGTH: 17
<212> TYPE: DNA
<213> ORGANISM: Canus lupus familiaris

<400> SEQUENCE: 13
ctgtgtttat agaaggg                                                   17

<210> SEQ ID NO 14
<211> LENGTH: 20
<212> TYPE: DNA
<213> ORGANISM: Canus lupus familiaris

<400> SEQUENCE: 14
agtagcctta taagggtgtg                                                20

<210> SEQ ID NO 15
<211> LENGTH: 17
<212> TYPE: DNA
<213> ORGANISM: Gallus gallus

<400> SEQUENCE: 15
ctgtgtttat agaaggg                                                   17

<210> SEQ ID NO 16
<211> LENGTH: 20
<212> TYPE: DNA
<213> ORGANISM: Gallus gallus

<400> SEQUENCE: 16
aggagccata taagggcaca                                                20
```